United States Patent [19]

Stec et al.

[11] Patent Number: 4,908,464

[45] Date of Patent: Mar. 13, 1990

[54] PROCESS FOR THE PRODUCTION OF 1,3,2-OXAZAPHOSPHORINANES

[75] Inventors: Wojciech J. Stec, Łódź; Czesław Radzikowski, Wrocław; Wiesław Szelejewski, Warsaw; Ryszard Kinas; Konrad Misiura, both of Łódź; Grzegorz Grynkiewicz; Jacek Grodner, both of Warsaw; Halina Kuśnierczyk, Wrocław; Andrzej Kutner, Warsaw; Sławomira Pilichowska, Łódź, all of Poland

[73] Assignees: Instytut Przemysłu Farmaceutycznego; Centrum Badeń Molekularnych i Makromolekularnych -PAN; Instytut Immunologii i Terapii Doswiadczalnej -PAN, all of Poland

[21] Appl. No.: 204,582

[22] Filed: Jun. 9, 1988

[30] Foreign Application Priority Data

Jun. 13, 1987 [PL] Poland .................................. 266240

[51] Int. Cl.[4] ............................................. C07F 9/24
[52] U.S. Cl. ...................................................... 558/81
[58] Field of Search ........................... 558/81; 564/488

[56] References Cited

FOREIGN PATENT DOCUMENTS 119971 6/1980 Poland .

OTHER PUBLICATIONS

K. Pankiewicz et al.; Synthesis and Absolute Configuration Assignment of Enantiomeric Forms of Ifosphamide, Sulfosphamide, and Trofosphamide; Dec. 19, 1979, of Journal of the American Chemical Society/101:26; pp. 7712–7718.

Wagner et al., "Synthetic Organic Chemistry", (1953), p. 660.

Primary Examiner—Anton H. Sutto

[57] ABSTRACT

Process for production of derivatives of 1,3,2-oxazaphosphorinane of general formula 1,

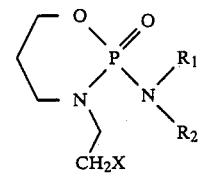

wherein $R_1$ and $R_2$ represent hydrogen atom or 2-halogenoalkyl group, and $R_1$ and $R_2$ are not at the same time hydrogen atoms, and X represents halogen atom is based, according to the invention, on the reduction of the respective 3-halogenoacyl derivatives of 1,3,2-oxazaphosphorinane of general formula 2,

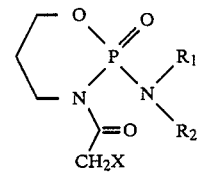

wherein the substituents have the above given meaning. The reduction is accomplished with the use of sodium borohydride in the presence of boron trifluoride etherate.

Derivatives that are prepared by the procedure described here demonstrate antitumor activity.

3 Claims, No Drawings

PROCESS FOR THE PRODUCTION OF 1,3,2-OXAZAPHOSPHORINANES

The present invention is related to the production of the derivatives of 1,3,2-oxazaphosphorinane of general formula 1,

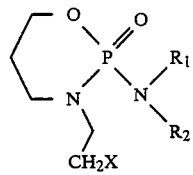

wherein $R_1$ and $R_2$ represent hydrogen atom or 2-halogenoalkyl group, and $R_1$ and $R_2$ are not at the same time hydrogen atoms, and X represents halogen atom.

From among this group of derivatives the compound of formula 1, where $R_1$ represents a hydrogen atom, $R_2$ a 2-chloroethyl group, and X a chlorine atom i.e. 3-(2-chloroethyl)-2-[(2-chloroethyl)-amino]-2-oxo-1,3,2-oxazaphosphorinane is an antitumor alkylating drug known as ifosfamide. On the other hand compounds of formula 1, where $R_1$ represents a hydrogen atom, $R_2$ a 2-chloroethyl group or bromoethyl group, and X is a chlorine or bromine atom, and X and halogen substituent at $R_2$ are not at the same time chlorine atoms, showed in preclinical studies more advantageous antitumor activity and higher therapeutic index than ifosfamide.

From the patent descriptions GB 1188159, FRG 2107936, U.S. Pat. Nos. 3,732,340 and 4,684,742 there are known methods for the preparation of the derivatives of 1,3,2-oxazaphosphorinane of general formula 1, containing 2-halogenoethyl substituent in 3 position of the ring that required the use as a substrate 3-aziridynopropanol or N-(2-chloroethyl)-3-aminopropanol and the properly substituted phosphoric acid dichloroanhydride. These methods, however, have a limited application, especially at the large scale, due to the properties of starting substances. More specifically, 3-aziridynopropanol is a cancerogenic substance, and N-(2-chloroethyl)-3-aminopropanol is not a chemically stable compound.

From the Polish Pat. No. 119971 there is known the method for the preparation of enantiomeric compounds of formula 1, wherein X represents a chlorine atom and one of the substituents $R_1$ or $R_2$ represents a chloroethyl group, that consists in the reduction of compound of formula 2,

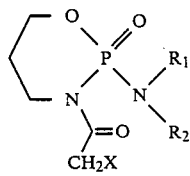

wherein substituents X, $R_1$ and $R_2$ have the above given meaning, with the use of boron hydride in tetrahydrofuran. In this method it is necessary to use the substrate of high purity and freshly prepared solution of boron hydride in tetrahydrofuran of a given concentration. However, the method does not provide repeatedly the same results, even when the given reaction procedure is strictly followed and the yields obtained do not exceed usually 50%.

It became unexpectedly evident that the reduction of compounds of formula 2 can be accomplished with the use of sodium borohydride provided that boron trifluoride etherate is also added to the reaction mixture. In this case boron trifluoride etherate works as a catalyst.

According to the present invention the reduction of the compounds of formula 2, where substituents have the above given meaning, is carried out with sodium borohydride, used in stoichiometric quantity, in the presence of boron trifluoride etherate in the medium of ether type neutral organic solvent, especially cyclic ethers, advantageously tetrahydrofuran and after the reaction is completed the product is isolated and purified in a usual way.

An advantageous result of the present invention is the high yield of the order of 75–90% and a good quality of the product obtained that can be easily purified by the known method.

Compounds of general formula 2 that are exploited in the present invention, except 2-[(2-chloroethyl)amino]-2-oxo-3-chloroacetyl-1,3,2-oxazaphosphorinane, are new and they have not been described in the literature. An efficient method of their preparation comprises the acylation of 2-(2-halogenoethyl)amino-2-oxo-1,3,2-oxazaphosphorinane, advantageously with halogenoacetic acid halide in the presence of a strong hydrogen bond acceptor, advantageously of phosphine oxide or trialkylphosphate, especially trimethylphosphate.

The present invention is illustrated by the following examples that do not limit its scope of application.

EXAMPLE I 3-(2-Chloroethyl)-2-[(2-chloroethyl)amino]-2-oxo-1,3,2-oxazaphosphorinane Sodium borohydride (2 g) was added to a vigorously stirred solution of 3-chloroacetyl-2-[(2-chloroethyl)amino]-2-oxo-1,3,2-oxzazaphosphorinane (10 g) in 75 mL of tetrahydrofuran followed by freshly distilled boron trifluoride etherate in 25 mL of tetrahydrofuran. The reaction mixture was maintained at 40° C. during the addition of reagents and for the next several minutes for the complete conversion of the substrate. To the reaction mixture 1 mL of ethanol was slowly added followed by 50 mL of water. The resulting solution was concentrated under reduced pressure to the final volume of 50 mL and extracted with ethylene chloride (3×50 mL). The extracts were pooled, dried with anhydrous $MgSO_4$ and concentrated. The resulting substance was purified by silica gel filtration and crystallized from ethyl ether to give 7.05 g (75% of theoretical yield) of colorless crystalline product, mp. 47°–49° C.; $^{31}$P-NMR (CHCl$_3$) δ 11.7 ppm (100%); TLC (CHCl$_3$-EtOH 9:1) $R_f$ 0.48.

EXAMPLE II 3-(-Bromoethyl)-2-[(2-bromoethyl)amino]-2-oxo-1,3,2-oxazaphosphorinane A solution of 18.8 mL of boron trifluoride etherate in 45 mL of tetrahydrofuran was added dropwise with stirring to the mixture of 18.0 g (49.5 mM) of 3-bromoacetyl-[(2-bromoethyl)amino]-2-oxo-1,3,2-oxazaphosphorinane and 4.09 g of sodium borohydride in 135 mL of anhydrous tetrahydrofuran at ambient temperature. The stirring was continued until all of the substrate was consumed (TLC) CHCl$_3$-acetone 3:1), $R_f$ 0.55). Then 180 mL of water was added to the reaction mixture. The resulting solution was concentrated under reduced pressure to the half of its original volume and extracted with chloroform (2×180 mL). The extract was dried with anh. MgSO$_4$ and concentrated in vacuo. The residue was crystallized from ethyl ether to give 14.0 g (81%) of colorless crystalline product, $^{31}$P-NMR (CHCl$_3$) δ 11.2 ppm (100%; TLC (CHCl$_3$-EtOH 9:1) R$_f$ 0.54; MS m/z 352 {[M+4]+, 0.8} 350 {[M+2]+, 2.2}, 348 {M+, 1.1}, 257 {[M+2-CH$_2$Br]+, 100}, 255 {[M-CH$_2$Br]+, 97}.

EXAMPLE III (+)-3-(2-Bromoethyl)-2-[(2-bromoethyl)amino]-2-oxo-1,3,2-oxazaphosphorinane Sodium borohydride (1.5 g) was added to the solution of 6.6 g (18.1 mM) of (+)-3-bromoacetyl-2[(2-bromoethyl)-amino]-2-oxo-1,3,2-oxazaphosphorinane {[α]$_D^{25}$ = +32.7° MeOH} in 45 mL of tetrahydrofuran at ambient temperature and then was added a solution of 5.2 mL of boron trifluoride etherate in 15 mL of tetrahydrofuran. The resulting suspension was stirred at room temperature until completed and then 15 mL of water was added. Following the isolation procedure described in Example II 5.7 g (90%) of the colorless crystalline product was obtained, mp. 93°–94.5° C.; $^{31}$P-NMR (CHCl$_3$) δ 11.2 ppm(100%), [α]$_D^{25}$ = +37.86 (c 16 MeOH); TLC-(CHCl$_3$-acetone 3:1) R$_f$ 0.2; MS as in example II

EXAMPLE IV 3-(2-Bromoethyl)-2-[(2-chloroethyl)amino]-2-oxo-1,3,2-oxazaphosphorinane Sodium borohydride (0.64 g) was added with stirring to the solution of 3.7 g (11.6 mM) of 3-bromoacetyl-[(2-chloroethyl)amino]-2-oxo-1,3,2-oxazaphosphorinane in 25 mL of tetrahydrofuran in room temperature and then 2.55 mL of boron trifluoride etherate in 5 mL of tetrahydrofuran was added dropwise. The suspension was stirred until completed, monitoring the progress of the reaction by TLC (CHCl$_3$-acetone 3:1, R$_f$ 0.55). Then 1 mL of methanol was added followed by 25 mL of water. The isolation procedure was as given in Example II.

Crystallization from ether-hexane gave 2.9 g (82%) of colorless crystalline product, mp.50°–51° C.;$^{31}$P-NMR (CHCl$_3$) δ 11.6 ppm (100%); TLC (CHCl$_3$-EtOH 9:1) R$_f$ 0.54; MS m/z 257 {[M+2-CH$_2$Cl]+, 2.6}, 255 {[M-CH$_2$Cl]+, 2.6}, 213 {[M+2-CH$_2$Br]+, 30}, 211 {[M-CH$_2$Br]+, 100}.

What we claim is:

1. A process for the preparation of the derivatives of 1,3,2-oxazaphosphorinane of general formula 1,

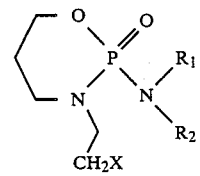

wherein R$_1$ and R$_2$ represent hydrogen atom or 2-halogenoalkyl group and R$_1$ and R$_2$ are not at the same time hydrogen atoms, and X represents halogen atom, which comprises reduction of the compound of general formula 2,

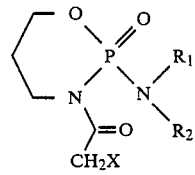

wherin substituents have the above given meaning, with sodium borohydride, used in a stoichiometric amount in the presence of boron trifluoride etherate in the medium of neutral ether type organic solvent, and isolation and purification of the product by a known method.

2. A process as claim in claim 1 wherein said organic solvent comprises cyclic ether.

3. A process as claim in claim 1 wherein said organic solvent is tetrahydrofuran.

* * * * *